United States Patent [19]

von Angerer

[11] Patent Number: 4,943,572

[45] Date of Patent: Jul. 24, 1990

[54] 1-CARBAMOYLALKYL-2-PHENYLINDOLES, PHARMACEUTICAL COMPOSITIONS AND USE

[75] Inventor: Erwin von Angerer, Grasslfing, Fed. Rep. of Germany

[73] Assignee: Schering Aktiengesellschaft, Berlin and Bergkamen, Fed. Rep. of Germany

[21] Appl. No.: 370,509

[22] Filed: Jun. 23, 1989

[30] Foreign Application Priority Data

Jun. 23, 1988 [DE] Fed. Rep. of Germany ....... 3821148

[51] Int. Cl.$^5$ ................. A61K 31/405; A61K 31/535; C07D 209/12; C07D 295/192
[52] U.S. Cl. ................. 514/235.2; 514/253; 514/323; 514/414; 514/415; 544/143; 544/144; 544/373; 546/201; 548/465; 548/511
[58] Field of Search ........... 544/143, 144, 373; 546/201; 548/465, 511; 514/235.2, 253, 323, 414, 415

[56] References Cited

U.S. PATENT DOCUMENTS 4,139,634 2/1979 Pigerol et al. ................. 548/511

*Primary Examiner*—Robert W. Ramsuer
*Attorney, Agent, or Firm*—Millen, White & Zelano

[57] ABSTRACT

Aminoalkylindoles of the formula

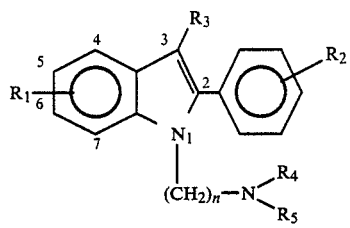

and 1-carbamoylalkyl-2-phenlindoles of the formula

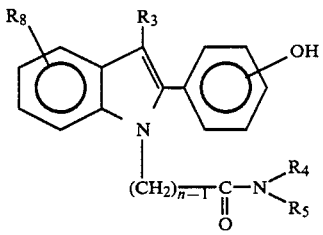

exhibit substantial estrogenic activity and a relatively low degree of anti-estrogenic activity.

6 Claims, No Drawings

1-CARBAMOYLALKYL-2-PHENYLINDOLES, PHARMACEUTICAL COMPOSITIONS AND USE

CROSS-REFERENCE TO RELATED APPLICATIONS

Indole derivatives are disclosed in applicants' earlier U.S. patent application Ser. No. 07/330,047, filed Mar. 29, 1989, based on a series of parent applications and claiming priority of German Application No. P 38 15 993.1, filed Apr. 13, 1981.

BACKGROUND OF THE INVENTION

The present invention relates to aminoalkylindoles, processes for their production, and pharmaceutical preparations containing same.

SUMMARY OF THE INVENTION

Objects of this invention are to provide novel chemical compounds, processes of making compounds, pharmaceutical preparations, and methods of administering such preparations.

Upon further study of the specification and appended claims, further objects and advantages of this invention will become apparent to those skilled in the art.

To attain such objects, there are provided aminoalkylindoles of Formula I

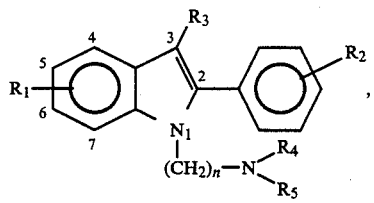

wherein $R_1$ is hydrogen, hydroxyl, or an alkanoyloxy group containing 1–10 carbon atoms, $R_2$ is a hydroxyl or an alkanoyloxy group containing 1–10 carbon atoms, $R_3$ is hydrogen or methyl, $R_4$, $R_5$, being the same or different, represent hydrogen, alkyl of 1–10 carbon atoms, aralkyl of 7–10 carbon atoms, or cycloalkyl of 3–7 carbon atoms, or $R_4$, $R_5$, with the inclusion of a single nitrogen atom or with the inclusion of a nitrogen and an oxygen atom or with the inclusion of two nitrogen atoms as heteroatoms, form a 5- or 6-membered heterocyclic ring, and n is an integer in the range of 4–15, inclusive, and the salts thereof are preferably physiologically acceptable salts of these compounds with acids.

Suitable as $R_1$ and $R_2$ alkanoyloxy groups are radicals of organic carboxylic acids containing 1–10 carbon atoms, which radicals can be saturated or unsaturated. They are derived from aliphatic, cycloaliphatic, aliphatic cycloaliphatic, cycloaliphatic aliphatic, and aromatic monocarboxylic acids. When a cyclic acid, the number of carbon atoms in the ring varies from 3 to 7, inclusive. The alkanoyloxy groups of acetic, propionic, butyric, isobutyric, pivalic, caproic, acrylic, crotonic, heptanoic, caprylic, pelargonic, decanoic, 3-cyclopentylpropionic, and benzoic acid are preferred as radicals $R_1$ and $R_2$.

The radical $R_1$ can be in the positions 4, 5, 6, or 7 of the indole ring system, with the 5-position being especially suitable.

The radical $R_2$ can be in the positions 2, 3, or 4 on the phenyl ring, when the position is the point of linkage to the 2-position of the indole system. Such compounds are especially pharmaceutically active when the radical $R_2$ is in the 4-position (para position).

Alkyl groups containing 1–10 carbon atoms and cycloalkyl groups of 3–7 carbon atoms are suitable as the $R_4$ and $R_5$ radicals.

Methyl, ethyl, propyl, butyl, pentyl, hexyl, heptyl, octyl, nonyl, and decanyl and isomers thereof are suitable as alkyl groups, and cyclopentyl and cyclohexyl are especially suitable as cycloalkyl groups.

Benzyl is a particular example of an aralkyl group represented by the $R_4$ and/or $R_5$ radicals.

The radicals $R_4$ and $R_5$ can be the same or different or can be components of a common ring. With the presence of a ring, the latter can contain, in addition to the nitrogen atom, an oxygen atom and a second nitrogen atom.

Particularly suitable as $R_4$ and $R_5$ radicals are the combination of hydrogen/methyl (derived from methylamino), hydrogen/hydrogen (derived from amino), and methyl/methyl (derived from dimethylamino), as well as the $(CH_2)_4$ radical (derived from pyrrolidino), the $(CH_2)_5$ radical (derived from piperidino), the $(CH_2)_2$—O—$(CH_2)_2$ radical (derived from morpholino), and the $(CH_2)_2$—NH—$(CH_2)_2$ radical (derived from piperazino).

The invention also relates to salts of compounds of Formula I. These salts can be both salts or inorganic and of organic acids. Especially suitable are the physiologically compatible salts, such as, for example, hydrochlorides, hydrobromides, acetates, malonates, and citrates.

The invention further relates to processes for the production of aminoalkylindoles of general Formula I. In this case, a compound of Formula IIa

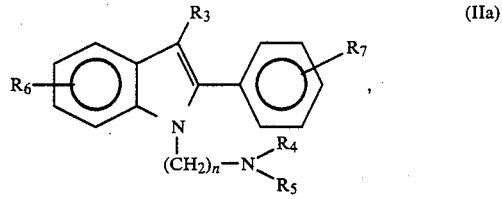

or of Formula IIb

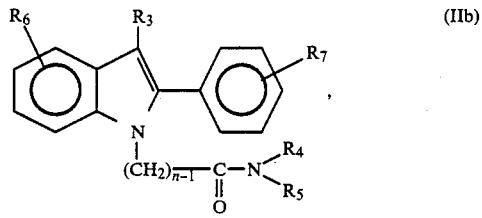

wherein $R_3$, $R_4$, $R_5$, and n have the same meaning specified in Formula I, $R_6$ is hydrogen or alkoxy containing 1–4 carbon atoms, and $R_7$ is alkoxy containing 1-4 carbon atoms is reacted under the conditions of an ether cleavage to a compound of Formula Ia

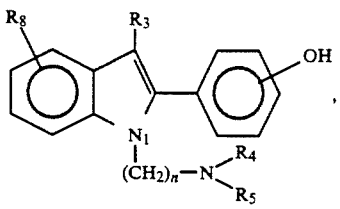

Alternatively, a compound of Formula IIIb

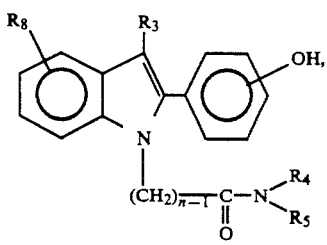

wherein $R_8$ is hydrogen or hydroxyl, the carbonyl function of the compound of Formula IIIb is completely reduced, and then the free aromatic hydroxyl group(s) is/are converted into an alkanoyloxy group having 1-10 carbon atoms.

A compound of Formula I is optionally converted with an organic or inorganic acid into the corresponding salt.

As alkoxy groups of the radicals $R_6$ and $R_7$, suitable are those having 1-4 carbon atoms, such as, for example, the methoxy, ethoxy, propoxy, isopropoxy, butoxy, isobutoxy, and tertbutoxy groups.

Those compounds of compound II, in which $R_6$ and $R_7$ represent alkoxy groups having 1-4 carbon atoms can be converted into the corresponding hydroxy groups of Formula I by ether cleavage. The ether cleavage takes place with or without a solvent. Boron tribromide, boron trifluoride, aluminum trichloride, silicon tetrachloride, aluminum tribromide, sodium methylthiolate, and trimthylsilyl iodide are suitable reagents for the ether cleavage. The reaction is generally performed at temperatures between −70° and 200° C. Inert solvents are suitable as solvents for this ether cleavage, for example, aliphatic halogenated hydrocarbons, e.g., methylene chloride; aromatic hydrocarbons, e.g., benzene, toluene, and xylene; halogenated aromatic hydrocarbons, e.g., chlorobenzene, dichlorobenzene; and dimethylformamide, as well as acetonitrile. Aliphatic ethers with alkyl radicals from 1-6 carbon atoms are also suitable.

Alternatively, the ether cleavage can also take place with the use of concentrated hydroiodic acid, pyridine hydrochloride, hydrobromic acid, and methyl magnesium iodide at temperatures between 20° and 250° C.

The processes usually used in chemistry for esterification are suitable for the optional subsequent esterification of the phenolic hydroxyl groups. For example, esterification can be conducted with a carboxylic acid or a carboxylic acid anhydride in the presence of strong acids, such as, for example, trifluoroacetic acid, perchloric acid, or p-toluenesulfonic acid, at room temperature, or at a somewhat elevated temperature. Similarly, the esterification can be conducted with a carboxylic acid anhydride in the presence of a tertiary amine at about 20°-80° C.

If pyridine and 4-dimethylaminopyridine are used together as tertiary amines, the esterification preferably can be performed at room temperature.

Any subsequent salt formation reaction is conducted under conventional conditions.

It has been found that compounds of Formula I and compounds of Formula IIIb have strongly anti-estrogenic properties.

Compounds with anti-estrogenic properties, i.e., materials which exhibit inhibitory activity against estrogens, have already been described in the literature.

Tamoxifen, for example, can be mentioned as an anti-estrogen (Eur.J. Cancer Clin. Oncol 1985, 21, 985, and J. S. Patterson, "10 Years of Tamoxifen in Breast Cancer," in *Hormonal Manipulation of Cancer: Peptides, Growth Factors and New (Anti) Steroidal Agents* (Raven Press: New York, 1987).

Steroidal anti-estrogens are described in European Patent Application No. 0138 504. Other anti-estrogens, which, like the present invention, relate to indole derivatives, have already been described in German Patent Specification No. 32 32 968, in J.Med.Chem. 1983, 26, 113; J.Med.Chem., 1984, 27, 1439; Eur.J. Cancer Clin. Oncol. 1985, 21, 531; and Cancer Treatment Reviews 1984, 11, 147. Hydroxylated 2-phenylindoles, which are present in the form of diamine platinum (II) complex compounds, are named in German Laid-Open Specification No. 37 30 746.

A disadvantage of the previously known anti-estrogens is that they also have a more or less strongly pronounced estrogenic activity, which is considered to be undesirable.

In contradistinction, the compounds of Formula I and Formula IIIb of the present invention exhibit strong anti-estrogenic activity, with only minimal residual estrogen activity.

The compounds of Formula I have a marked affinity for the estradiol receptor and competitively displace $^3H$-$17\beta$ estradiol from the receptor.

In vivo, they exhibit strong anti-estrogenic effects on the mouse uterus and inhibit the estrogen-stimulated uterus growth up to 100 percent. Conversely, estrogen activity cannot be detected or can be detected only to a small extent in these tests. Of particular important is that these compounds have an inhibiting effect on the growth of hormone-dependent tumor cells, especially on the growth of estrogen-dependent human breast tumor cells (MCF-7).

Thus, the compounds according to the invention are suitable for therapy of estrogen-dependent diseases, for example, anovular infertility, prostatic hyperplasia, breast cancer, endometrium cancer, and melanoma.

The following pharmacological tests show the action of the compounds according to the invention.

Table 1 shows an overall view of the tested compounds of Formula I and their relative binding affinity (RBA*) for the estrogen receptor from calf uterus, relative to $17\beta$ estradiol=100.

The test protocol is described in Cancer Treatment Reviews 1984, 11, 147.

From Table 1 it can be seen that compounds 2, 3, 6, and 8 exhibit the greatest affinity in comparison with estradiol. In this tested series, compound 7 exhibited the least affinity for the estrogen receptor.

TABLE 1

Tested compounds of formula I and their relative binding affinities for the estrogen receptor

[Chemical structure: indole core with HO-phenyl, R3 substituent, 2-(4-hydroxyphenyl), and N-(CH2)n-NR4R5]

| Compound | n | $R_3$ | $R_4$ | $R_5$ | RBA* |
|---|---|---|---|---|---|
| 1 | 4 | $CH_3$ | —$(CH_2)_4$— | | 3.6 |
| 2 | 6 | $CH_3$ | H | H | 25 |
| 3 | 6 | $CH_3$ | $CH_3$ | H | 27 |
| 4 | 6 | $CH_3$ | $CH_3$ | $CH_3$ | 12 |
| 5 | 6 | H | —$(CH_2)_4$— | | 2.3 |
| 6 | 6 | $CH_3$ | —$(CH_2)_4$— | | 21 |
| 7 | 6 | H | —$(CH_2)_5$— | | 1.3 |
| 8 | 6 | $CH_3$ | —$(CH_2)_5$— | | 23 |
| 9 | 8 | $CH_3$ | —$(CH_2)_4$— | | 7.6 |
| 10 | 6 | $CH_3$ | —$(CH_2)_2$—O—$(CH_2)_2$— | | 10 |
| 11 | 6 | $CH_3$ | $C_2H_5$ | $C_2H_5$ | 14 |
| 12 | 6 | $CH_3$ | $CH_2C_6H_5$ | H | 15 |

*Relative binding affinities for the estrogen receptor from calf uterus, relative to 17beta estradiol = 100

Table 2 shows the estrogen and anti-estrogen activities of compounds 1, 2, 3, and 6, as well as 10, 11, and 12. These activities were found in an in vivo test on the infantile mouse. This test is fully described in Cancer Treatment Reviews 1984, 11, 147, and J.Med.Chem., 1984, 27, 1439. From Table 2, it can be seen that all tabulated compounds exhibit a strong to very strong estrogen antagonistic effect. An estrogen intrinsic activity is hardly detectable in all the tested derivatives, with the exception of compound 3, 11, and 12 at the highest tabulated dosages.

TABLE 2

Uterotrophic and antiuterotrophic action on infantile mouse

| Cmpd | Dose (ug) | Uterotrophic Test Rel. uterus wgt | Antiuterotrophic Rel. uterus wgt | Test Inhib. (%) |
|---|---|---|---|---|
| Control | | 7.7 ± 2.5 | | |
| 1 | 1 | 7.6 ± 2.8 | 43.7 ± 8.2 | 5 |
| | 5 | 8.0 ± 3.1 | 47.6 ± 10.5 | |
| | 25 | 6.4 ± 1.1 | 16.2 ± 4.6 | 78 |
| | 125 | 6.4 ± 1.3 | 25.5 ± 7.9 | 53 |
| Estrone | 0.4 | 45.8 ± 6.2 | | |
| Control | | 15.9 ± 3.6 | | |
| 2 | 1 | 10.9 ± 4.7 | | |
| | 5 | 12.0 ± 2.2 | 30.0 ± 9.1 | 68 |
| | 25 | 12.4 ± 2.7 | 15.1 ± 1.2 | 102 |
| | 125 | 16.9 ± 2.7 | 16.2 ± 2.7 | 99 |
| 3 | 1 | 14.2 ± 3.1 | | |
| | 5 | 22.8 ± 8.6 | 38.1 ± 8.2 | 49 |
| | 25 | | 41.0 ± 8.5 | 43 |
| | 125 | 34.0 ± 6.3 | 33.8 ± 2.4 | 59 |
| Estrone | 0.4 | 59.8 ± 20.0 | | |
| Control | | 15.5 ± 2.9 | | |
| 6 | 1 | 12.5 ± 1.7 | 45.8 ± 3.2 | 20 |
| | 5 | 9.0 ± 1.8 | 15.4 ± 1.7 | 100 |
| | 25 | 13.9 ± 2.8 | 14.4 ± 2.2 | 103 |
| | 125 | | 8.9 ± 1.6 | 117 |
| Estrone | 0.4 | 53.4 ± 3.6 | | |
| Control | | 11.5 ± 3.6 | | |
| 6 | 1 | | 48.3 ± 7.2 | |
| | 5 | | 20.1 ± 7.3 | 73 |
| | 25 | | 12.6 ± 1.9 | 97 |
| | 50 | 8.2 ± 1.8 | | |
| | 250 | 12.7 ± 2.7 | | |
| Estrone | 0.4 | 43.0 ± 7.2 | | |
| Control | | 18.8 ± 9.6 | | 18.8 ± 9.6 | |
| 10 | 1 | 21.2 ± 3.9 | | | |
| | 5 | 19.5 ± 6.9 | 5 | 51.2 ± 7.5 | 8 |
| | 25 | 21.8 ± 11.3 | 25 | 47.7 ± 8.4 | 18 |
| | 125 | 17.4 ± 1.7 | 125 | 18.0 ± 4.8 | 102 |
| Estrone | 0.4 | 54.2 ± 12.1 | 0.4 | 54.2 ± 12.1 | |

| | Dose ug/ animal | Action | Dose ug/ animal | Action | Inhib. (%) |
|---|---|---|---|---|---|
| Control | | 25.4 ± 14.5 | | 25.4 ± 14.5 | |
| 11 | 5 | 24.8 ± 11.7 | 5 | 51.3 ± 4.9 | 11 |
| | 25 | 14.7 ± 4.3 | 25 | 52.1 ± 8.9 | 8 |
| | 125 | 19.8 ± 3.3 | 125 | 40.0 ± 4.7 | 50 |
| | 625 | 36.4 ± 17.6 | 625 | 43.7 ± 7.4 | 37 |
| Estrone | 0.4 | 54.6 ± 6.5 | 0.4 | 54.6 ± 6.5 | |
| Control | | 18.2 ± 5.5 | | 18.2 ± 5.5 | |
| | 5 | 17.8 ± 4.6 | 5 | 53.2 ± 9.0 | 25 |
| | 25 | 23.6 ± 2.5 | 25 | 44.6 ± 7.1 | 43 |
| | 125 | 34.0 ± 7.2 | 125 | 40.8 ± 8.7 | 51 |
| | | | 625 | 41.8 ± 7.4 | 49 |
| Estrone | 0.4 | 64.7 ± 8.7 | 0.4 | 64.7 ± 8.7 | |

Table 3 shows the results of research on the cytostatic activity of compounds 1 and 6 in comparison with tamoxifen.

On the hormone-sensitive human MCF-7 breast cells, a strong inhibition of the cell growth, determined by cell count and [$^3$H] thymidine incorporation, was found in the DNA. With concentrations of $10^{-7}$M, a significant lowering of the cell count and of the thymidine incorporation was found six days after incubation. Under the same conditions, tamoxifen exhibited no significant effect.

The test protocol for the research is fully described in Eur.J. Cancer Clin. Oncol. 1985, 21, 531.

TABLE 3

Action of 1 and 6 on the growth of hormone-dependent human MCF-7 breast cancer cells

| Cmpd. | Concn. (M) | Cell Count (% T/C) | [$^3$H] Thymidine incorporation (% T/C) |
|---|---|---|---|
| 1 | $1 \times 10^{-7}$ | 106 | 67 |
| | $5 \times 10^{-7}$ | 84 | 76 |
| | $1 \times 10^{-6}$ | 94 | 85 |
| | $5 \times 10^{-6}$ | 62 | 74 |
| 6 | $1 \times 10^{-7}$ | 65 | 32 |
| | $5 \times 10^{-7}$ | 49 | 32 |
| | $1 \times 10^{-6}$ | 24 | 22 |
| | $5 \times 10^{-6}$ | 12 | 3 |
| 8 | $1 \times 10^{-7}$ | 48 | |
| | $1 \times 10^{-6}$ | 44 | |
| | $1 \times 10^{-5}$ | 38 | |
| 10 | $1 \times 10^{-7}$ | 75 | |
| | $1 \times 10^{-6}$ | 52 | |
| | $1 \times 10^{-5}$ | 36 | |
| 12 | $1 \times 10^{-7}$ | 47 | |
| | $1 \times 10^{-6}$ | 46 | |
| | $1 \times 10^{-5}$ | 41 | |
| Tamoxifen | $1 \times 10^{-7}$ | 77 | 71 |
| | $1 \times 10^{-6}$ | 27 | 27 |

Tables 4, 5, and 6 show, analogously to Tables 1, 2, and 3, the corresponding data for the tested 1-carbamoylalkyl-2-phenylindoles of general Formula IIIb.

As can be seen from Table 5, these compounds not only exhibit marked anti-estrogenity, but at high dosages also have a significant estrogen activity.

TABLE 4

Tested 1-carbamoylalkyl-2-phenylindoles of General Formula IIIb and Their Formula IIIb and Their Relative Binding Affinities for the Estrogen Receptor

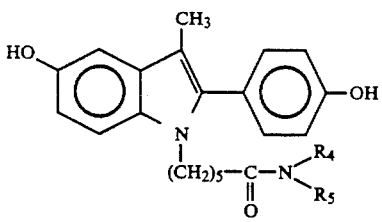

| Compound | $R_4$ | $R_5$ | RBA |
|---|---|---|---|
| 16 | —(CH$_2$)$_4$— | | 7 |
| 17 | —(CH$_2$)$_5$— | | 19 |
| 18 | —(CH$_2$)$_2$—O—(CH$_2$)$_2$— | | 26 |
| 19 | C$_2$H$_5$ | C$_2$H$_5$ | 15 |
| 20 | CH$_2$C$_6$H$_5$ | H | 12 |

TABLE 5

Uterotrophic and antiuterotrophic action of 1-carbamoylalkyl-2-phenylindoles of general formula IIIb on infantile mouse

| | Uterotrophic Test | | Antiuterotrophic Test | | |
|---|---|---|---|---|---|
| Compound | Dose: ug/animal | Action | Dose: ug/animal | Action | Inhib. (%) |
| Control | | 21.9 ± 2.7 | | 21.9 ± 2.7 | |
| 16 | 5 | 18.2 ± 2.3 | 5 | 47.5 ± 10.9 | 10 |
| | 25 | 16.5 ± 2.4 | 25 | 42.0 ± 7.0 | 29 |
| | 125 | 17.7 ± 0.9 | 125 | 35.2 ± 5.5 | 53 |
| | 625 | 35.3 ± 10.7 | 625 | 40.7 ± 3.9 | 44 |
| Estrone Control | 0.4 | 50.2 ± 3.1 | 0.4 | 50.2 ± 3.1 | |
| 17 | | 14.4 ± 2.5 | | 14.4 ± 2.5 | |
| | 1 | 23.8 ± 2.8 | | | |
| | 5 | 17.7 ± 3.2 | 5 | 48.7 ± 9.1 | 6 |
| | 25 | 16.3 ± 3.0 | 25 | 42.9 ± 4.7 | 22 |
| | 125 | 18.6 ± 2.5 | 125 | 29.5 ± 2.7 | 59 |
| Estrone Control | 0.4 | 50.8 ± 7.3 | 0.4 | 50.8 ± 7.3 | |
| 18 | | 18.8 ± 9.6 | | 18.8 ± 9.6 | |
| | 1 | 20.2 ± 3.4 | | | |
| | 5 | 22.0 ± 5.6 | 5 | 53.5 ± 8.7 | |
| | 25 | 21.2 ± 4.6 | 25 | 52.8 ± 7.4 | |
| | 125 | 43.0 ± 8.2 | 125 | 39.8 ± 18.1 | 41 |
| Estrone Control | 0.4 | 54.2 ± 12.1 | 0.4 | 54.2 ± 12.1 | |
| 19 | 5 | 18.4 ± 3.2 | 5 | 50.9 ± 8.2 | 13 |
| | 25 | 17.9 ± 2.0 | 25 | 50.9 ± 4.8 | 13 |
| | 125 | 17.6 ± 2.6 | 125 | 44.5 ± 6.2 | 34 |
| | 625 | 32.7 ± 6.5 | 625 | 35.3 ± 6.1 | 66 |
| Estrone Control | 0.4 | 54.6 ± 6.5 | 0.4 | 54.6 ± 6.5 | |
| 20 | | 15.6 ± 5.8 | | 15.6 ± 5.8 | |
| | 5 | 16.5 ± 3.6 | 5 | 50.7 ± 5.0 | |
| | 25 | 20.9 ± 6.5 | 25 | 46.9 ± 7.7 | 12 |
| | 125 | 16.7 ± 3.9 | 125 | 50.3 ± 4.6 | |
| | 625 | 19.9 ± 4.1 | 625 | 59.5 ± 12.4 | −23 |
| Estrone | 0.4 | 51.2 ± 5.9 | 0.4 | 51.2 ± 5.9 | |

TABLE 6

Action of 1-carbamoylalkyl-2-phenylindoles of general formula IIIb on the growth of hormone-dependent human MCF-7 breast cancer cells

| Compound | Concentration (M): | Cell Count (% T/C) |
|---|---|---|
| 16 | 1·10$^{-7}$ | 57.2 ± 4.4 |
| | 5·10$^{-7}$ | 48.2 ± 5.4 |
| | 1·10$^{-6}$ | 47.1 ± 3.7 |
| | 5·10$^{-6}$ | 44.0 ± 3.6 |
| | 1·10$^{-5}$ | 42.1 ± 4.0 |
| 17 | 1·10$^{-7}$ | 89.0 ± 10.8 |
| | 5·10$^{-7}$ | 95.5 ± 10.2 |

TABLE 6-continued

Action of 1-carbamoylalkyl-2-phenylindoles of general formula IIIb on the growth of hormone-dependent human MCF-7 breast cancer cells

| Compound | Concentration (M): | Cell Count (% T/C) |
|---|---|---|
| | 1·10$^{-6}$ | 96.0 ± 7.7 |
| | 5·10$^{-6}$ | 99.6 ± 7.6 |
| | 1·10$^{-5}$ | 86.5 ± 8.3 |
| 18 | 1·10$^{-7}$ | 57.5 ± 6.8 |
| | 5·10$^{-7}$ | 58.1 ± 6.7 |
| | 1·10$^{-6}$ | 56.4 ± 5.2 |
| | 5·10$^{-6}$ | 42.4 ± 3.7 |
| | 1·10$^{-5}$ | 33.3 ± 2.8 |
| 19 | 1·10$^{-7}$ | 59.7 ± 6.1 |
| | 5·10$^{-7}$ | 60.1 ± 3.8 |
| | 1·10$^{-6}$ | 61.4 ± 4.4 |
| | 5·10$^{-6}$ | 56.2 ± 4.5 |
| | 1·10$^{-5}$ | 44.9 ± 3.7 |
| 20 | 1·10$^{-7}$ | 58.3 ± 4.9 |
| | 5·10$^{-7}$ | 47.9 ± 3.0 |
| | 1·10$^{-6}$ | 46.8 ± 4.2 |
| | 5·10$^{-6}$ | 36.6 ± 2.5 |
| | 1·10$^{-5}$ | 26.8 ± 4.2 |

The invention also relates to pharmaceutical preparations which contain at least one compound of general Formulas I or IIIb, as well as their salts, and the use of these compounds for treatment of estrogen-dependent diseases and tumors.

The compounds according to the invention are suitable for production of pharmaceutical compositions and preparations. The pharmaceutical compositions or pharmaceutical agents contain as an active ingredient one or more of the compounds according to the invention, optionally in mixture with other pharmacologically or pharmaceutically active materials. The production of the pharmaceutical agents takes place in a known way, and the known and usual pharmaceutical auxiliary agents, as well as other usual vehicles and diluents, can be used.

Suitable as such vehicles and auxiliary agents are, for example, those that are recommended or indicated in the following literature passages as auxiliary agents for pharmacy, cosmetics, and related fields: Ullmans Encyklopaedie der technischen Chemie [Ullman's Encyclopedia of Industrial Chemistry], Vol. 4 (1953), pp. 1–39; Journal of Pharmaceutical Sciences, Vol. 52 (1963), p. 918 ff.; H.v. Czetsch-Lindewald, Hilfsstoffe fuer Pharmazie und angrenzende Gebiete [Auxiliary Agents for Pharmacy and Related Fields], Pharm. Ind., No. 2, 1961, p. 72 ff.; Dr. H. P. Fiedler, Lexikon der Hilfstoffe fuer Pharmazie, Kosmetik und angrenzende Gebiete [Lexicon of Auxiliary Agents for Pharmacy, Cosmetics and Related Fields], Cantor KG. Aulendorf in Wuerttemberg 1971.

The compounds can be administered orally or parenterally, e.g., intraperitoneally, intramuscularly, subcutaneously, or percutaneously. The compounds can also be implanted in the tissue. The amount of the compound to be administered fluctuates within a wide range. As a function of the condition to be treated and the type of administration, the amount of administered compound can generally be 0.01–100 mg/kg of body weight, preferably 0.1–20 mg/kg of body weight, per day. Guidelines for determining particularly preferred dosage ranges within said ranges can be found in literature for treating specific conditions with specific anti-estrogenic agents of known activity. In a given case, a clinician of ordinary skill in the art can determine the optimum dosage ranges by conventional and routine experimentation.

Capsules, pills, tablets, dragees, etc. are suitable for oral administration. Besides the active ingredient, the dosage units can contain a pharmaceutically compatible vehicle such as, for example, starch sugar, sorbitol, gelatin, lubricant, silicic, acid, talc, etc. The individual dosage units for oral application can contain, for example, 10 to 100 mg of the active ingredient.

For parenteral administration, the active ingredients can be dissolved or suspended in a physiologically compatible diluent. As diluents, very often oils, with or without addition of a solubilizer, surfactant, or suspending or emulsifying agent, can be used. For example, olive, peanut, cottonseed, soybean, castor and sesame oils can be used.

The compounds can also be used in the form of a depot injection or an implantation preparation, which can be formulated so that a delayed active ingredient release is made possible.

Production of Starting Materials

The starting products of general Formula IIa or IIb to be used for the production of the compounds according to the invention of general Formula I are obtained either by:

(a) N-alkylation of the corresponding 1H-2-phenylindole compound X with the corresponding $\alpha,\Omega$-dibromoalkane Br—(CH$_2$)—Br and subsequent exchange of the omega-BR atom with the NR$_4$R$_5$ group, or (b) reaction of the corresponding 1H-2-phenylindole compound X—after deprotonation—with the corresponding omega-bromoalkylcarbonamide

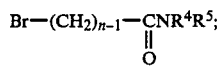

the latter compounds are easily available by reaction of the corresponding omega-bromocarboxylic acid chloride

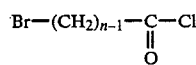

with an excess of amine HNR$_4$R$_5$.

A1. General Directions for N-alkylation 1.44 g (0.06 mol) of sodium is dissolved at −70° in 200 ml of liquid ammonia. After disappearance of the blue coloring, a solution consisting of 0.035 mol of the corresponding 1H-2-phenylindole compound X (J.Med.-Chem. 1984, 24, 1439) in 100 ml of tetrahydrofuran is added to this solution. After 30 minutes stirring time, a solution of 0.042 mol of alpha,omega-dibromoalkane Br—(CH$_2$)$_n$—Br dissolved in 20 ml of tetrahydrofuran is slowly distilled in the reaction mixture. It is stirred for 30 minutes more, and the cooling bath is removed. After evaporation of the ammonia, the remaining residue is mixed with water and extracted with ether. After separation of the phases, the organic solution is dried and concentrated by evaporation in a vacuum, and the remaining residue is recrystallized from ethanol or purified by column chromatography.

The N-alkyl compounds Ya to Ye thus produced are summarized in Table 7.

TABLE 7

N-Alkyl Compounds Ya to Ye by Alkylation of Corresponding 1H-2-phenylindole Compounds X

| N-Alkyl Compound Y | 1H-2-Phenylindole X | | | Br(—CH$_2$)$_n$Br | Melt. point |
|---|---|---|---|---|---|
| | R$_3$ | R$_6$ | R$_7$ | n | |
| Ya 5-methoxy-2-(4-methoxyphenyl)-3-methyl-1-(4-bromobutyl)-indole | CH$_3$ | OCH$_3$ | OCH$_3$ | 4 | 59–60 |
| Yb 5-methoxy-2-(4-methoxyphenyl)-3-methyl-1-(6-bromohexyl)-indole | CH$_3$ | OCH$_3$ | OCH$_3$ | 6 | 60 |
| Yc 5-methoxy-2-(4-methoxyphenyl)-1-(6-bromohexyl)-indole | H | OCH$_3$ | OCH$_3$ | 6 | 82* |
| Yd 5-methoxy-2-(4-methoxyphenyl)-3-methyl-1-(8-bromooctyl)-indole | CH$_3$ | OCH$_3$ | OCH$_3$ | 8 | oil |
| Ye 2-(4-methoxyphenyl)-3-methyl-1-(6-bromohexyl)-indole | CH$_3$ | H | OCH$_3$ | 6 | oil |

*uncertain

A2. General Directions for Preparation of the Compounds of General Formula IIa by Exchange of the Omega-Bromine Atom in the Alkyl Side Chain (a) Reaction with a Cyclic Amine A solution of 3.0 mmol of the corresponding omega-bromoalkylindole Y is heated in 100–150 ml of the cyclic amine for 4 hours to 120° C. After cooling to room temperature, it is shaken out with dichloromethane and water, the combined organic phases are on magnesium sulfate, and the solvent is distilled off. The raw products accumulating as brown oil are chromatographed on silica gel with methanol or methanol/triethylamine (1:1 to 1:3).

(b) Reaction with Phthalimide-Potassium/Hydrazine 8.0 mmol of 1-(omega-bromoalkyl)-indole compound Y and 8.8 mmol of phthalimide/potassium are refluxed in 100 ml of anhydrous dimethylformamide for 2 hours. After cooling, it is shaken out with dichloromethane and water. Then it is dried on sodium sulfate, and the solvent is distilled off. The residue is chromatographed on silica gel with dichloromethane/ethyl acetate (10:1). For release of the amine, it is taken up in 50 ml of ethanol (99 percent) and mixed with hydrazine hydrate in 20 ml of ethanol. It is refluxed for 2 hours; after cooling, is acidified (pH 2–3) with 40 ml of 2 n hydrochloric acid;

and the precipitate is suctioned off. After distilling off of the solvent, it is adjusted to be alkaline (pH 8–9) with 40 ml of 2 n sodium hydroxide solution and extracted three times with 50 ml of ethyl acetate each. Then it is dried on sodium sulfate and chromatographed on silica gel with dichloroethane/trimethylamine (5:1).

(c) Reaction with an Aliphatic Amine 7.0 mmol of 1-(omega-bromoalkyl)-indole compound Y is dissolved in 30 ml of ethanol (99 percent), mixed with 40 ml of 40 percent aqueous solution of the aliphatic amine, and refluxed for 3 hours. After cooling, the ethanol is mostly removed, and the residue is taken up in 100 ml of dichloromethane and extracted with 100 ml of water. Then the organic phase is dried on magnesium sulfate, and the solvent is distilled off. The residue is chromatographed on silica gel with methanol.

Compounds IIa, produced according to directions A2.(a), A2.(b), and A2.(c) are set forth in Table 8.

B. General Directions for Production of the Compounds of General Formula IIb by Reaction of 1H-2 Phenylindoles X With Omega-Bromoalkylcarbonamides

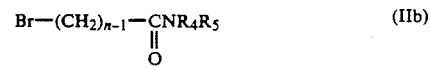

In a reaction flask, 20.0 mmol of NaH in paraffin under nitrogen is freed of the paraffin by multiple washing with ether and mixed with 20 ml of dry dimethylacetamide. A solution of 14 mmol of 1H-2-phenylindole X in 80 ml of dry dimethylacetamide is instilled into this mixture under cooling with ice. After 30 minutes of stirring under ice cooling, a solution of 15 mmol of omega-bromoalkylcarbonamide in 60 ml of dry dimethylacetamide is instilled. After 2 hours of stirring at room temperature, the NaH excess is carefully destroyed with water. The reaction mixture is extracted several times with ethyl acetate. The combined organic phases are washed with water, dried on $Na_2SO_4$, and freed of solvent. The products are purified by column chromatography.

Compounds IIb, produced according to the above directions, are set forth in Table 9.

TABLE 8

| | Compounds of general formula IIa from N-(omega-bromoalkyl)indoles Y | | | | |
|---|---|---|---|---|---|
| Compound of general formula IIa | N-($\omega$-bromoalkyl) indole Y | Amine $HNR_4R_5$ | Direction | Appearance | Yield (%) |
| IIa1 5-Methoxy-2-(4-methoxyphenyl)-3-methyl-1-[4-pyrrolidino-butyl]-indole | Ya | Pyrrolidine | A2a | colorless crystals mp 59–60° C. | 51 |
| IIa2 5-Methoxy-2-(4-methoxyphenyl)-3-methyl-1-[6-aminohexyl]-indole | Yb | Hydrazine | A2b | pale yellow oil | ? |
| IIa3 5-Methoxy-2-(4-methoxyphenyl)-3-methyl-1-[6-methylaminohexyl]-indole | Yb | Methylamine | A2c | pale yellow oil | 84 |
| IIa4 5-Methoxy-2-(4-methoxyphenyl)-3-methyl-1-[6-dimethylaminohexyl]-indole | Yb | Dimethylamine | A2c | pale yellow oil | 41 |
| IIa5 5-Methoxy-2-(4-methoxyphenyl)-1-[6-pyrrolidino-hexyl]-indole | Yc | Pyrrolidine | A2a | pale yellow oil | 77 |
| IIa6 5-Methoxy-2-(4-methoxyphenyl)-3-methyl-1-[6-pyrrolidinohexyl]-indole | Yb | Pyrrolidine | A2a | yellow oil | 90 |
| IIa7 5-Methoxy-2-(4-methoxyphenyl)-1-[6-piperidino-hexyl]-indole | Yc | Piperidine | A2a | pale yellow oil | 90 |
| IIa8 5-Methoxy-2-(4-methoxyphenyl)-3-methyl-1-[6-piperidino-hexyl]-indole | Yb | Piperidine | A2a | pale yellow oil | 89 |
| IIa9 5-Methoxy-2-(4-methoxyphenyl)-3-methyl-1-[8-pyrrolidino-octyl]-indole | Yd | Pyrrolidine | A2a | yellow oil | 65 |
| IIa13 2-(4-Methoxyphenyl)-3-methyl-1-[6-pyrrolidino-hexyl]-indole | Ye | Pyrrolidine | A2a | pale yellow oil | 75 |

TABLE 9

| | Compounds of general formula IIb from 1-H-phenylindoles X | | | | |
|---|---|---|---|---|---|
| | | 1H-2-Phenylindol X | | | |
| Compounds of general formula IIb | | $R_3$ | $R_6$ | $R_7$ | $\omega$-Bromoalkyl-carbonamide | Appearance/melting point |
| IIb 16 5-Methoxy-2-(4-methoxyphenyl)-3-methyl-1-(6-pyrrolidino-carbonylpentyl)-indole | | $CH_3$ | $OCH_3$ | $OCH_3$ | 6-bromohexanoyl-pyrrolidine | yellow resin |
| IIb 17 5-Methoxy-2-(4-methoxyphenyl)-3-methyl-1-(6-piperidino-carbonylpentyl)-indole | | $CH_3$ | $OCH_3$ | $OCH_3$ | 6-bromohexanoyl-piperidine | bright yellow |
| IIb 18 5-Methoxy-2-(4-methoxypentyl)-3-methyl-1-(6-morpholinocarbonylpentyl)-indole | | $CH_3$ | $OCH_3$ | $OCH_3$ | 6-bromohexanoyl-morpholine | bright brown resin |

TABLE 9-continued

| | Compounds of general formula IIb from 1-H-phenylindoles X | | | | |
|---|---|---|---|---|---|
| | | 1H-2-Phenylindol X | | | |
| Compounds of general formula IIb | | $R_3$ | $R_6$ | $R_7$ | ω-Bromoalkyl-carbonamide | Appearance/melting point |
| IIb 19 | 1-(6-Diethylcarbamoylpentyl)-5-methoxy-2-(4-methoxyphenyl)-3-methylindole | $CH_3$ | $OCH_3$ | $OCH_3$ | 6-bromohexamoyl-diethylamine | colorless resin |
| IIb 20 | 1-(6-Benzylcarbamoylpentyl)-5-methoxy-2-(4-methoxyphenyl)-3-methylindole | $CH_3$ | $OCH_3$ | $OCH_3$ | M-(6-bromo-hexanoyl)-benzyl-amine | melting point (ethanol) 127–129 |

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire texts of all applications, patents, and publications, cited above and below, and of corresponding West German Application No. P 38 21 148.3, filed June 23, 1988, are hereby incorporated by reference.

EXAMPLES

EXAMPLES 1–20

C1. General Directions for Production of the Compounds of General Formula Ia (i.e., compounds of General Formula I, which exhibit at least one free hydroxy group) and IIb by Ether Cleavage of IIa or IIb Under a nitrogen atmosphere and with ice cooling, there is dissolved 4.0 mmol of indole derivative IIa or IIb in 100 ml of anhydrous dichloromethane. It is stirred for about 10 minutes more, and 9.0 mmol (2.25 g, 0.85 ml) of boron tribromide, dissolved in 3 ml of absolute dichloromethane, is instilled. It is now stirred for 30 minutes with ice cooling and 2–3 hours at room temperature. With renewed ice cooling, 20 ml of ethyl acetate is instilled and stirred for 30 minutes at room temperature. It is shaken out at least three times with 50 ml each of ethyl acetate, 10 percent sodium bicarbonate solution, and water. The combined organic phases are dried on magnesium sulfate, and the resultant dried phases are dissolved in ethanol and then crystallized in a freezer. The colorless to yellow-brown products obtained of general Formula Ia or IIIb are suctioned off, washed several times with water, and dried in a desiccator on phosphorus pentoxide.

The compounds of general Formula Ia, thus produced, are shown in Table 10, and those of general Formula IIIb are shown in Table 11.

C2. General Directions for Esterification of Compounds of General Formula Ia 12.3 mmol of the compound of general Formula Ia is dissolved in 50 ml of methylene chloride, mixed with 20 ml of the corresponding acid anhydride or acid halide and 10 ml of pyridine and stirred overnight. Then it is put into 200 ml of water, extracted with methylene chloride, dried, and concentrated by evaporation in a vacuum.

C3. General Directions for Production of the Hydrochloride of a Compound of General Formula I First, a compound of general Formula Ia, as described in C2, is esterified. The oily residue remaining after concentration by evaporation of the methylene chloride extract is dissolved in 200 ml of ether; hydrochloric acid gas is conducted through this solution for 30 minutes. The resulting precipitate is suctioned off and dried.

TABLE 10

| Example/Compound | Compound of general formula I | Starting Product | Directions | Appearance | Mp [°C.] | Yield [%] |
|---|---|---|---|---|---|---|
| 1 | 5-Hydroxy-2-(4-hydroxyphenyl)-3-methyl-1-[4-pyrrolidino-butyl]-indole | IIa 1 | C1 | Beige Crystals | 148 (decom) | 35 |
| 2 | 5-Hydroxy-2-(4-hydroxyphenyl)-3-methyl-1-[6-amino-hexyl]-indole | IIa 2 | C1 | Yellow crystals | >139 (decom) | 76 |
| 3 | 5-Hydroxy-2-(4-hydroxyphenyl)-3-methyl-1-[6-methylamino-hexyl]-indole | IIa 3 | C1 | Yellow crystals | 194 (decom) | 24 |
| 4 | 5-Hydroxy-2-(4-hydroxyphenyl)-3-methyl-1-[6-dimethylamino-hexyl]-indole | IIa 4 | C1 | Yellow crystals | 189 (decom) | 73 |
| 5 | 5-Hydroxy-2-(4-hydroxyphenyl)-1-[6-pyrrolidino-hexyl]-indole | IIa 5 | C1 | Yellow crystals | 109–112 (decom) | 50 |
| 6 | 5-Hydroxy-2-(4-hydroxyphenyl)-3-methyl-1-[6-pyrrolidino-hexyl]-indole | IIa 6/IIb 16 | C1 | Beige crystals | 148–150 (decom) | 56 |
| 7 | 5-Hydroxy-2-(4-hydroxyphenyl)-1-[6-piperidino-hexyl]-indole | IIa 7 | C1 | Reddish brown crystals | 125–128 (decom) | 80 |
| 8 | 5-Hydroxy-2-(4-hydroxyphenyl)-3-methyl-1-[6-piperidino-hexyl]-indole | IIa 8/IIb 17 | C1 | Yellow crystals | 102 (decomp) | 23 |
| 9 | 5-Hydroxy-2-(4-hydroxyphenyl)-3-methyl-1-[8-pyrrolidino-ocytl]-indole | IIa 9 | C1 | Yellow crystals | 166–169 (decomp) | 42 |
| 10 | 5-Hydroxy-2-(4-hydroxyphenyl)-3-methyl-1-[6-morpholino-hexyl]-indole | IIb 18 | C1 | ? | 107–110 (decomp) | ? |
| 11 | 1-(6-Diethylaminohexyl)-5-hydroxy-2-hydroxyphenyl)-3-methyl-indole | IIb 19 | C1 | bright yellow amorphous powder | ? | ? |
| 12 | 1-(6-Benzylaminohexyl)-5-hydroxy-2-(4-hydroxyphenyl)-3-methyl-indole | IIb 20 | C1 | beige amorphous | ? | ? |

TABLE 10-continued

| Example/ Compound | Compound of general formula I | Starting Product | Directions | Appearance | Mp [°C.] | Yield [%] |
|---|---|---|---|---|---|---|
| 13 | 2-(4-Hydroxyphenyl)-3-methyl-1-[6-pyrrolidino-hexyl]-indole | IIa 13 | C1 | powder Yellow crystals | ? | 35 |
| 14 | 5-Acetoxy-2-(4-acetoxyphenyl)-3-methyl-1-[6-piperidino-hexyl]-indole | Compound 7 + Acetic anhydride | C2 | yellow oil | — | 53 |
| 15 | 5-Benzoyloxy-2-(4-benzoyloxyphenyl)-3-methyl-1-[6-piperidino-hexyl]-indole Hydrochlorid | Compound 7 + Benzoyl chloride | C3 | Pale yellow oil | — | 55 |

TABLE 11

| Example/ compound | Compound of general formula IIIb | Starting product | Apperance | Mp (°C.) |
|---|---|---|---|---|
| 16 | 5-Hydroxy-2-(4-hydrdoxyphenyl)-3-methyl-1-(6-pyrrolidinocarbonylpentyl)-indole | IIb 16 | bright green amorphous powder | ? |
| 17 | 5-Hydroxy-2-(4-hydroxyphenyl)-3-methyl-1-(6-pyrrolidinocarbonylpentyl)-indole | IIb 17 | orange amorphous powder | 83–94 |
| 18 | 5-Hydroxy-2-(4-hydroxyphenyl)-3-methyl-1-(6-morpholinocarbonylpentyl)-indole | IIb 18 | bright yellow amorphous powder | ? |
| 19 | 1-(6-Diethylcarbamoylpentyl)-5-hydroxy-2-(4-hydroxyphenyl)-3-methylindole | IIb 19 | yellowish amorphous powder | ? |
| 20 | 1-(6-Benzylcarbamoylpentyl)-5-hydroxy-2-(4-hydroxyphenyl)-3-methylindole | IIb 20 | ? | 189–191 |

EXAMPLES 21-23

The following Examples 21–23 are pharmaceutical formulations of some compounds according to the invention.

EXAMPLE 21

21 g of 5-hydroxy-2-(4-hydrophenyl)-1-(6-pyrrolidinohexyl]-indole and 89.0 g of lactose are homogeneously mixed and, in each 210 mg of this mixture is poured into resin gelatin, two-piece capsules of size 3.

EXAMPLE 22

Tablets can be produced in the usual way from the following components:

| | |
|---|---|
| 50 mg | of 5-hydroxy-2-(4-hydrophenyl)-3-methyl-1-(6-pyrrolidino-hexyl]-indole |
| 200 mg | of lactose |
| 200 mg | of microcrystalline cellulose |
| 50 mg | of magnesium stearate |
| 500 mg | total weight of tablets |

EXAMPLE 23

Tablets can be produced in the usual way from the following components:

| | |
|---|---|
| 10 mg | of 5-hydroxy-2-(4-hydrophenyl)-3-methyl-1-(8-pyrrolidino-octyl]-indole |
| 220 mg | of lactose |
| 220 mg | of microcrystalline cellulose |
| 50 mg | of magnesium stearate |
| 500 mg | of total weight of tablets |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. 1-Carbamoylalkyl-2-phenylindoles of formula IIIb

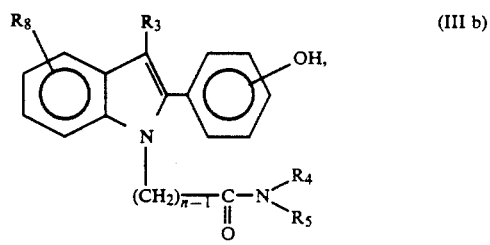

(III b)

2. A compound according to claim 1:
   5-hydroxy-2-(4-hydroxyphenyl)-3-methyl-1-(6-pyrrolidinocarbonylpentyl)-indole,
   5-hydroxy-2-(4-hydroxyphenyl)-3-methyl-1-(6-piperidinocarbonylpentyl)-indole,
   5-hydroxy-2-(4-hydroxyphenyl)-3-methyl-1-(6-morpholinocarbonylpentyl)-indole,
   1-(6-diethylcarbamoylpentyl)-5-hydroxy-2-(4-hydroxyphenyl)-3-methylindole, or
   1-(6-benzylcarbamoylpentyl)-5-hydroxy-2-(4-hydroxyphenyl)-3-methylindole.

3. A pharmaceutical preparation comprising a pharmaceutical carrier and a compound according to claim 4.

4. A pharmaceutical preparation comprising a pharmaceutical carrier and a compound according to claim 2.

5. A method of treating an estrogen-dependent disease comprising adminstering an anti-estrogenically effective dosage of a compound according to claim 1.

6. A method of treating an estrogen-dependent disease comprising adminstering an anti-estrogenically effective dosage of a compound according to claim 2.

UNITED STATES PATENT AND TRADEMARK OFFICE
CERTIFICATE OF CORRECTION

PATENT NO. : 4,943,572

DATED : July 24, 1990

INVENTOR(S) : Erwin von ANGERER

It is certified that error appears in the above-identified patent and that said Letters Patent is hereby corrected as shown below:

Column 16, claim 1, following the formula (III b):

Please add the following "$R_3$ is hydrogen or methyl, $R_4$ and $R_5$ are each hydrogen, alkyl of 1-10 carbon atoms, aralkyl of 7-10 carbon atoms, or cycloalkyl of 3-7 carbon atoms, or $R_4$ and $R_5$, together with one or two nitrogen atoms, or a nitrogen and an oxygen atom, represent a 5- or 6-membered heterocyclic ring, $R_8$ is hydrogen, or hydroxyl, and n=4-15, or an acid salt thereof."

UNITED STATES PATENT AND TRADEMARK OFFICE
CERTIFICATE OF CORRECTION

PATENT NO. : 4,943,572

DATED : July 24, 1990

INVENTOR(S) : Erwin von ANGERER

It is certified that error appears in the above-identified patent and that said Letters Patent is hereby corrected as shown below:

Column 16, claim 3, line 59:

reads "4"

should read -- 1 --

Signed and Sealed this

Twenty-fourth Day of September, 1991

Attest:

HARRY F. MANBECK, JR.

Attesting Officer

Commissioner of Patents and Trademarks